United States Patent [19]

Hannart

[11] 4,218,453

[45] Aug. 19, 1980

[54] N-SUBSTITUTED HEXAHYDRO-6-CANTHINONES FOR TREATING CARDIO-CIRCULATORY, CEREBROVASCULAR, AND RESPIRATORY DYSFUNCTION

[76] Inventor: Jean A. A. J. Hannart, 98, Avenue De Fré, Brussels, Belgium

[21] Appl. No.: 826,857

[22] Filed: Aug. 22, 1977

[30] Foreign Application Priority Data

Aug. 26, 1976 [FR] France .................................. 76 25802
May 31, 1977 [FR] France .................................. 77 16546

[51] Int. Cl.² .................... A61K 31/445; C07D 471/06
[52] U.S. Cl. ............................ 424/256; 260/326.13 B; 546/66; 546/85; 546/86
[58] Field of Search ...................... 260/293.53, 293.55, 260/296 P, 295 A; 424/256; 546/66

[56] References Cited

FOREIGN PATENT DOCUMENTS 853435 10/1977 Belgium ..................................... 546/66

OTHER PUBLICATIONS

Taborsky, R., et al., *J. Med. Chem.*, 7, 135–141, (1964).
Laronze, J., Dr. of Science Thesis, Reims, 12/18/74.
Yates, P. et al., *J. Am. Chem. Soc.*, 95, 7842–7850, (1973).
March, J., Advanced Organic Chemistry, McGraw Hill, New York, 1968, pp. 335–336.

*Primary Examiner*—John M. Ford
*Assistant Examiner*—Richard A. Schwartz

[57] ABSTRACT

The invention relates to new products, in the form of bases or salts, derivatives of hexahydro-6-canthinone which may be substituted and are represented by the general formula:

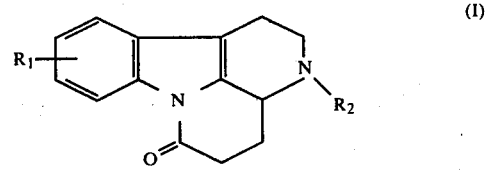

(I)

in which $R_1$ represents a hydrogen atom or hydroxy, $C_1$–$C_5$ alkyl, $C_2$–$C_5$ acyloxy, methoxy or halo radical and $R_2$ represents a hydrogen atom or straight or branched $C_1$–$C_5$ alkyl radical with the proviso that $R_1$ is not hydrogen or hydroxy in the 8-position when $R_2$ is methyl or $R_1$ is not methoxy in the 10-position when $R_2$ is hydrogen. The new products are especially useful for treating cardio-circulatory, cerebro-vascular and respiratory insufficiencies.

The invention also relates to a process in which the hexahydro-6-canthinone compounds are obtained by treating a $N_b$-alkyltryptamine with β-formylpropionic acid in an aromatic hydrocarbon at the reflux temperature of the reaction medium.

5 Claims, No Drawings

N-SUBSTITUTED HEXAHYDRO-6-CANTHINONES FOR TREATING CARDIO-CIRCULATORY, CEREBROVASCULAR, AND RESPIRATORY DYSFUNCTION

The present invention relates to N-substituted and unsubstituted hexahydro-6-canthinone derivatives, their preparation and use as pharmaceutical drugs in the form either of their free bases or their acid addition salts formed with pharmaceutically acceptable inorganic and organic acids, for example those which provide a halide, e.g. chloride anion or a sulphate or phosphate anion or an acetate, citrate, succinate, arabogalactate sulphate, or pamoate ion.

These compounds may be represented by the following general formula:

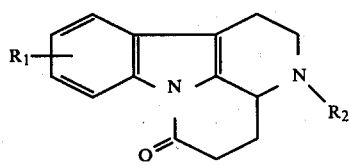
(I)

In the above formula:
$R_1$ represents either a hydrogen atom or a hydroxy, acyloxy, carbamate or methoxy radical or a halogen atom;
$R_2$ represents either a hydrogen atom or a linear or branched lower alkyl radical containing 1–5 carbon atoms or a $CH_2$—$CH_2$—X chain in which X represents a heteroatom such as oxygen or nitrogen, which heteroatom may in its turn be bonded to one or more hydrogen atoms or to one or more alkyl substituents which contain 1–5 carbon atoms.

The derivative of formula I wherein $R_1$ means H and $R_2$ means $CH_3$ (reference OC-330) is known to have been prepared and described by J.-Y. Laronze (Dr. of Science Thesis, Reims, Dec. 18, 1974).

The derivative of formula I wherein $R_1$ means 8-OH and $R_2$ means $CH_3$ (reference OC-332) is known to have been prepared and described by P. Yates et al, J. Amer. Chem. Soc., 95, 7842 (1973).

The derivative of formula I wherein $R_1$ means 10-methoxy and $R_2$ means hydrogen is also known, see Journal of Medicinal Chemistry (1964), 135–141.

The compounds of formula I are prepared among others by the following general method described in the aforementioned publication of P. Yates et al.

According to said known process, a $N_b$-alkyltryptamine compound of the formula

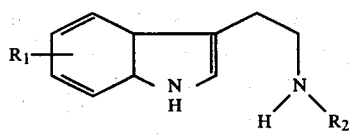
(II)

wherein $R_1$ and $R_2$ have the above-indicated meanings is condensed with a compound of the formula

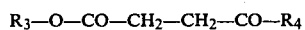
$R_3$—O—CO—$CH_2$—$CH_2$—CO—$R_4$ (II')

wherein $R_3$ may inter alia represent a methyl or ethyl group and $R_4$ may inter alia represent a halogen atom to obtain a N-2-(indolyl-3-ethyl)-succinamic acid ester of the formula

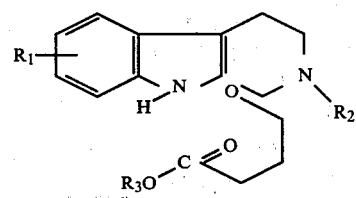
(III)

wherein $R_1$, $R_2$ and $R_3$ have the previously given meanings.

Thereafter, the ester of formula III is cyclized to form a tricyclic derivative of the formula

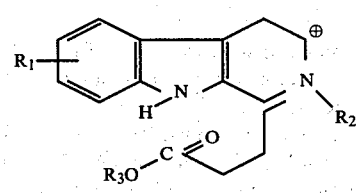
(IV)

wherein $R_1$, $R_2$ and $R_3$ have the previously given meanings and the derivative of formula IV is reduced to 1,2,3,4-tetrahydro-1-(2-carboalkoxyethyl)-$\beta$-carboline which may be substituted and has the formula

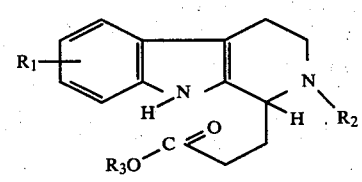
(V)

wherein $R_1$, $R_2$ and $R_3$ have the above indicated meanings.

The compound of formula V is finally cyclized to a compound of formula I.

Applicant has found that the ester of formula III can be obtained in less time and easier by condensing the tryptamine compound of formula II with succinic anhydride instead of the compound of formula II' to thus obtain a N-2-(indolyl-3-ethyl) succinamic acid, i.e. a compound of formula III wherein $R_3$ represents a hydrogen atom and esterifying said acid to an ester of formula III wherein $R_3$ represents a methyl or ethyl group.

Advantageously, condensation of the tryptamine compound of formula II with succinic anhydride takes place in an anhydrous benzene medium under reflux heating conditions.

In a second step, the substituted succinic acid of formula III is esterified by means of either diazomethane or a solution of hydrochloric acid in anhydrous methanol or ethanol.

In a third step, the ester of formula III ($R_3$=$CH_3$ or $C_2H_5$) is treated by a reagent such as phosphorus oxychloride which is known to cause the reaction called cyclization of BISCHLER NAPIERALSKI, to form the tricyclic compound of formula IV which is immediately reduced in the reaction medium by means of a alkaline borohydride to form the ester of formula V according to the following equation:

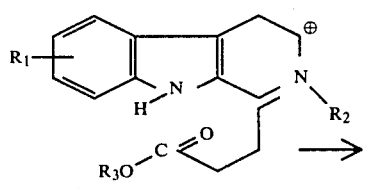

(IV)

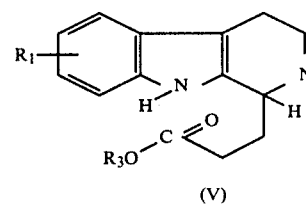

(V)

In a fourth and last step, the ester of formula V as a free base or still better after transformation into a salt such as a hydrochloride is heated in the presence of a reagent such as polyphosphoric acid or dicyclohexylcarbodiimide dissolved in benzene which is known to cause cyclisation to lactame and leads to the compounds of the general formula I.

According to another embodiment, the tricyclic derivative of formula IV is transformed into a tetracyclic derivative of formula VI by causing the reaction medium to become alkaline, e.g. by means of an aqueous solution of sodium hydroxyde, and then reduced by means of an alkali metal borohydride to form a derivative of the general formula I.

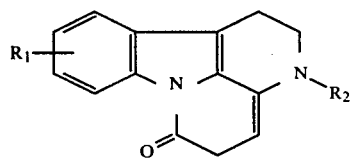

(VI)

According to still another embodiment of this invention, in one single step, a N$_b$-alkyltryptamine of formula II wherein R$_1$ and R$_2$ are as defined previously, is condensed with β-formylpropionic acid in an aromatic hydrocarbon such as benzene or toluene. After reflux heating during 4–5 hours, the solvent is evaporated and the residue after having been dissolved in acetic acid is heated under reflux conditions during 2 hours after which the solution is diluted with water and once again heated under reflux conditions for 2 hours. Once the reaction is ended, the reaction medium is cooled, diluted with water, made alkaline or basic with sodium or potassium hydroxide and then extracted with an organic solvent. By evaporation and crystallization, one obtains the desired compound of general formula I.

This reaction may be represented as follows:

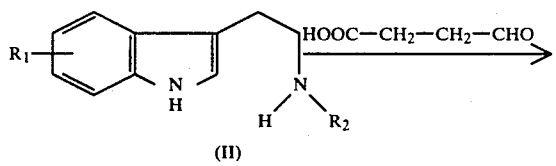

(II)

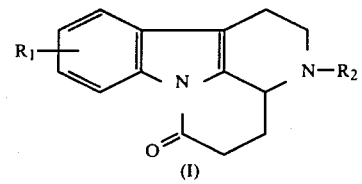

(I)

Said compound of formula I also may be obtained by condensation of a N$_b$-alkyltryptamine with α-ketoglutaric acid. The tetrahydro-β-carboline (III) thus obtained is then cyclisated in a hydrochloric acid solution in methanol. Such process is disclosed in G. Hahn, Ber., 71 2163 (1938), R. G. Taborsky and N. H. Mc Isaac J. Med. Chem. 135 (1964) and may be represented as follows:

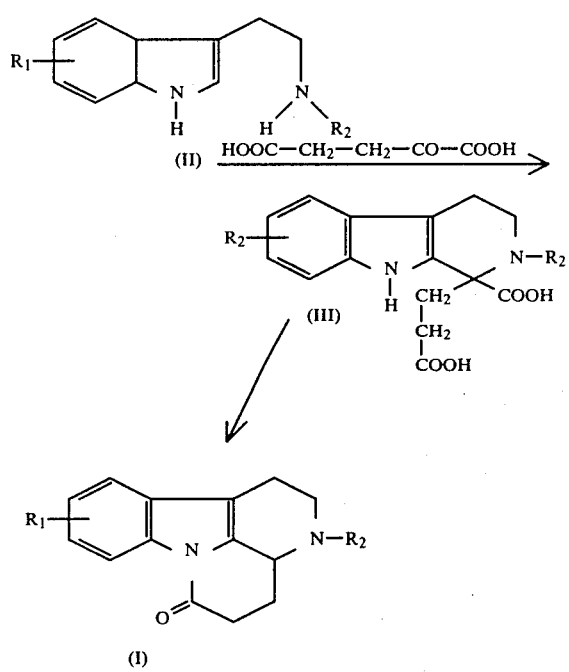

The examples given hereinafter now illustrate the preparation of the compounds according to the present invention without restricting the latter.

EXAMPLE 1

Preparation of 3-ethyl-1,2,3,3a,4,5-hexahydro-6-canthinone (ref. OC-331); (formula I: R$_1$=H; R$_2$=C$_2$H$_5$) by the first process embodiment.

(a) N-2-(indolyl-3-ethyl)-N-ethylsuccinamic acid (formula III: R$_1$=R$_3$=H; R$_2$=C$_2$H$_5$)

4.2 g of N$_b$-ethyltryptamine (formula II R$_1$=H; R$_2$=C$_2$H$_5$) and 3.3 g of succinic anhydride are suspended in 500 ml anhydrous benzene. The mixture is heated under reflux conditions for 1 h. 30 min. The benzene is evaporated under vacuum and the dry residue is dissolved in an aqueous solution of 20% sodium carbonate. The aqueous solution is then washed with methylene chloride, acidified by means of concentrated hydrochloric acid and extracted with methylene chloride. The organic phase is washed with water, dried on anhydrous sodium sulphate and evaporated to dryness. One obtains 5.1 g of product which is crystallized from acetone.

m.p.: 102° C.
U.V. spectrum:
(c=4.9 $10^{-3}$ g/l)
neutral methanol: 222 (4.54); 270 (3.72) 281 (3.82); 290 (3.75)
I.R. spectrum: (KBr): bands at 1730 and 1620 cm$^{-1}$
Mass spectrum: M$^+$ calcultated for $C_{16}H_{20}O_3N_2=288$; found 288
N.M.R. spectrum:
two singlets of 1 proton at 10.2 and 8.6 ppm
two singlets of 2 protons at 2.7 and 2.4 ppm
one triplet of 3 protons at 1.13 ppm
a group of 5 protons centered on 7.4 ppm

| Analysis : | % C | % H | % N |
|---|---|---|---|
| Calculated | | | |
| ($C_{16}H_{20}O_3N_2$) | 66.64 | 6.99 | 9.71 |
| Found | 66.61 | 6.97 | 9.68 |

(b) Methyl ester of N-2(indolyl-3-ethyl)-N-ethylsuccinamic acid (formula III: $R_1=H$; $R_2=C_2H_5$; $R_3=CH_3$)

4.9 g of acid prepared in step a hereabove are dissolved in 150 ml of a methanol solution of hydrochloric acid. After one hour, the reaction is completed. The methanol is evaporated in the cold state and the oily residue left is diluted with 100 ml of water. The solution is then extracted with methylene chloride, the organic phase is washed successively with a 5% sodium carbonate solution, water dried with anhydrous sodium sulphate and evaporated to dryness under vacuum. The residue is crystallized from acetone. One obtains 5.1 g of methyl ester.

m.p.: 85° C.
U.V. spectrum:
(c=4.6 $10^{-3}$ g/l)
neutral methanol 222 (4.57); 275 (3.7) 283 (3.76); 290 (3.7)
I.R. spectrum:
(KBr) bands at 1740 and 1630 cm$^{-1}$
Mass spectrum:
M$^+$ calculated for $C_{17}H_{22}O_3N_2=302$ found 302
N.M.R. spectrum:
one singlet of 1 proton at 8.9 ppm
two singlets of 2 protons at 2.73 and 2.53 ppm
one doubled singlet of 3 protons at 3.75 ppm
one triplet of 3 protons at 1.16 ppm
a group of 5 protons centered on 7.4 ppm

| Analysis : | % C | % H | % N |
|---|---|---|---|
| Calculated | | | |
| ($C_{17}H_{22}O_3N_2$) | 67.52 | 7.33 | 9.26 |
| Found | 67.57 | 7.31 | 9.21 |

(c) 1,2,3,4-tetrahydro-1-(2-carbomethoxyethyl)-2-ethyl-β-carboline (hydrochloride) (formula V: $R_1=H$; $R_2=C_2H_5$; $R_3=CH_3$)

5 g of methyl ester are suspended into 300 ml of anhydrous benzene. 21 ml of phosphorus oxychloride are added and the mixture is heated under reflux conditions in argon for 5 hours. The mixture is then evaporated to dryness and the residue is taken up with 250 ml of absolute ethanol and 9 g of sodium borohydride are added in small batches. Once the reaction is finished, one adds 250 ml of water and the solution is extracted with methylene chloride. The organic phase is washed with water, dried and evaporated to dryness.

One obtains 5.5 g of the product of formula V ($R_1=H$; $R_2=C_2H_5$; $R_3=H$) as an oily base. Said base is taken up with methanol and made acid with hydrochloric acid. This gives 4.2 g of the desired product of formula V in the form of its hydrochloride as crystals m.p. 218° C. (decomposition).

The free base has the following characteristics:
U.V. spectrum:
(c=4.5 $10^{-3}$ g/l)
neutral methanol 239 (4.28); 264 (3.96); 290 (3.66); 300 (3.66)
I.R. spectrum:
(KBr): bands at 1710 cm$^{-1}$
Mass spectrum:
M$^+$ calculated for $C_{17}H_{22}O_2N_2$: 286; Found 286
N.M.R. spectrum:
one singlet of 1 proton at 8.3 ppm
one singlet of 3 protons at 3.8 ppm
one triplet of 3 protons at 1.2 ppm
one group of 4 protons centered on 7.3 ppm

| Analysis : | % C | % H | % N |
|---|---|---|---|
| Calculated | | | |
| ($C_{17}H_{22}O_2N_2$) | 71.31 | 7.74 | 9.78 |
| Found | 71.29 | 7.71 | 9.76 |

(d) 3-ethyl-1,2,3,3a,4,5-hexahydro-6-canthinone (formula I: $R_1=H$; $R_2=C_2H_5$)

To 4 g of β-carboline derivative, 25 ml of polyphosphoric acid are added and the mixture is stirred to give a homogeneous solution. Said solution is left for 20 hours at room temperature in a blanket of argon. The mixture is then poured into ice-cold water, made alkaline and extracted with methylene chloride. The organic extraction phase is washed, dried and evaporated to dryness under vacuum to give 2.5 g of the desired product of formula I ($R_1=H$; $R_2=C_2H_5$) as an oily base. Said base is taken up with methanol and acidified with hydrochloric acid to form 2.3 g of crystallized hydrochloride, m.p. 275° C. (decomposition).

The base has the following characteristics:
U.V. spectrum:
(c=5.12 $10^{-3}$ g/l) (HCl)
neutral methanol 239 (4.27); 262 (3.96); 291 (3.68); 300 (3.72)
I.R. spectrum:
(KBr) band at 1700 cm$^{-1}$
Mass spectrum:
M$^+$ calculated for $C_{16}H_{18}ON_2=254$ Found 254
N.M.R. spectrum:
one triplet of 1 proton at 8.45 ppm
one triplet of 3 protons at 1.2 ppm
one group of 3 protons centered at 7.35 ppm

| Analysis : | % C | % H | % N |
|---|---|---|---|
| Calculated | | | |
| ($C_{16}H_{18}ON_2$) | 75.56 | 7.13 | 11.01 |
| Found | 75.54 | 7.10 | 11.06 |

EXAMPLE 2

One single step process embodiment for preparing 3-ethyl-1,2,3,3a,4,5-hexahydro-6-canthinone (formula I: $R_1=H$; $R_2=C_2H_5$)

19 g of $N_b$-ethyltryptamine and 11.2 g of β-formyl-propionic acid are dissolved into 800 ml of anhydrous benzene and heated under reflux conditions in nitrogen blanket for 4 h. 30 min. with azeotropic distillation of water. The benzene is then evaporated to dryness and the residue is taken up into one liter of acetic acid and heated under reflux conditions in nitrogen blanket for 1 hour 30 min.

One adds 500 ml of water and the reflux heating is continued for 2 hours.

The solution is then cooled and after two liters of water have been added, the mixture is made alkaline by means of 30% sodium hydroxide and extracted with methylene chloride.

The organic extraction phase is washed, dried and evaporated to dryness under vacuum to leave 24.6 g of the desired product of formula I in its base form.

Said base is taken up with methanol and acidified with hydrochloric acid to give 23.9 g of crystallized hydrochloride m.p. 275° C. (decomposition). Yield 81.4%.

EXAMPLES 3-7

The following compounds have been prepared by anyone of the previously described methods:

3-propyl-1,2,3,3a,4,5-hexahydro-6-canthinone (formula I: $R_1=H$; $R_2=C_3H_7$)

U.V. spectrum:
(c=5.07 $10^{-3}$ g/l) (HCl) neutral methanol
λ (log. ε): 240 (4.32); 290 (3.77); 300 (3.75); 264 (4.07)
I.R. spectrum (KBr):
band at 1710 cm$^{-1}$
Mass spectrum:
M$^+$ calculated for $C_{17}H_{20}ON_2$: 268; found: 268
N.M.R. spectrum:
one triplet of 1 proton at 8.5 ppm
one group of 3 protons at 7.2-7.5 ppm
one triplet of 3 protons at 0.93 ppm 3-butyl-1,2,3,3a,4,5-hexahydro-6-canthinone (formula I: $R_1=H$; $R_2=C_4H_9$)

U.V. spectrum:
(c=5.32 $10^{-3}$ g/l) (HCl) neutral methanol
λ (log. ε): 239 (4.66); 262 (3.98); 290 (3.52); 299 (3.54)
I.R. spectrum (KBr):
band at 1715 cm$^{-1}$
Mass spectrum:
M$^+$ calculated for $C_{18}H_{22}ON_2$: 282 found: 282
N.M.R. spectrum:
one triplet of 1 proton at 8.46 ppm
one group of 3 protons at 7.2-7.5 ppm
one group of 3 protons at 0.75-1 ppm 3-isopropyl-1,2,3,3a,4,5-hexahydro-6-canthinone (formula I: $R_1=H$; $R_2=$iso $C_3H_7$)

U.V. spectrum (c=5.17 $10^{-3}$ g/l) (HCl) neutral methanol
λ (log. ε): 241 (4.29); 265 (3.98); 293 (3.51); 303 (3.49)
I.R. spectrum (KBr):
band at 1720 cm$^{-1}$
Mass spectrum:
M$^+$ calculated for $C_{17}H_{20}ON_2$: 268; found: 268
N.M.R. spectrum:
one triplet of 1 proton at 8.5 ppm
one group of 3 protons at 7.2-7.5 ppm
one doublet of 3 protons at 1.3 ppm ($J_{AB}=7$ cps)
one doublet of 3 protons at 1 ppm ($J_{AB}=7$ cps)

10-methyl-3-ethyl-1,2,3,3a,4,5-hexahydro-6-canthinone (formula I: $R_1=CH_3$; $R_2=C_2H_5$)

U.V. spectrum: (c=5.12 $10^{-3}$ g/l) (HCl) neutral methanol
λ (log. ε): 245 (4.36); 266 (4); 295 (3.71); 303 (3.72)
I.R. Spectrum (KBr):
band at 1710 cm$^{-1}$
Mass spectrum:
M$^+$ calculated for $C_{17}H_{20}ON_2$: 268 found: 268
N.M.R. spectrum:
one doublet of 1 proton at 8.33 ppm (J=8 cps)
one singlet of 1 proton ($H_{11}$) at 7.28 ppm
one doublet of 1 proton ($H_9$) at 7.2 ppm (J=8 cps)
one singlet of 3 protons at 2.5 ppm
one triplet of 3 protons at 1.2 ppm 10-chloro-3-ethyl-1,2,3,3a,4,5-hexahydro-6-canthinone (formula I: $R_1=Cl$; $R_2=C_2H_5$)

U.V. spectrum (c=5.16 $10^{-3}$ g/l) (tartrate) neutral methanol
λ (log. ε): 245 (4.44); 271 (4.04); 296 (3.61); 306 (3.55)
Mass spectrum:
M$^+$ calculated for $C_{16}H_{17}N_2OCl$: 288 found: 288
I.R. spectrum (KBr):
band at 1710 cm$^{-1}$
N.M.R. spectrum:
one doublet of 1 proton ($H_8$) at 8.26 ppm (J=8 cps)
one singlet of 1 proton ($H_{11}$) at 7.33 ppm
one doublet of 1 proton ($H_9$) at 7.23 ppm (J=8 cps)
one triplet of 3 protons at 1.2 ppm The invention also relates to the industrial applications and inter alia the pharmaceutical uses of the above described products. As a matter of fact, most of the compounds of formula I have been subjected to pharmaceutical tests which showed interesting properties. The control substance was vincamine.

Acute toxicity

The compounds of the invention and vincamine also were administered by intragastric route to Charles River stock mice. The lethal doses for 50% (LD$_{50}$) were determined graphically according to the method of Lichtfield and Wilcoxon (J. Pharmacol. Exp. Therap. 1946, 96, 99).

The results are summarized in Table I.

TABLE I

| Compound | LD$_{50}$ mg/kg p.o. |
|---|---|
| Vincamine | 970 |
| OC - 330 | 310 |
| OC - 331 | 411 |
| OC - 332 | 527 |

Hypobaric anoxia test on mice.

Charles River stock mice of the same sex, weighting about 20±2 g are shared into three lots of 10 animals each. The lots 1 and 2 comprise treated animals, i.e. those having received either a substance to be tested or vincamine, together with solvent, at 1 ml/100 g of body weight. The third lot comprises control animals i.e. those having only received solvent at 1 ml/100 g of body weight.

The compounds examined were administered by intragastric route 15 minutes before the experiment. The doses as applied correspond to 1/5, 1/10, 1/20 of the $LD_{50}$ for the compounds of the invention and 1/5 of $LD_{50}$ for vincamine.

The animals were placed in an atmosphere impoverished in oxygen by creating a partial vacuum (190 mm Hg, corresponding to 5.25% oxygen), in about 30 seconds.

The survival time of the mice was measured with a chronometer. Said time is increased by the agents capable of enhancing oxygenation of tissues and more particularly brain oxygenation.

The percentages of survival time increase with respect to the values obtained for the control animals are calculated.

The effects obtained with the compounds of formula I compared with vincamine are summarized in tables II, III and IV.

TABLE II

| Lot | OC - 330 Survival time (sec.) | Variation % |
|---|---|---|
| 1st experiment | | |
| Control | 39 (± 2) | |
| OC - 330 | | |
| (60 mg/kg or $LD_{50}/5$ | 122 (± 4) | + 212 |
| Vincamine | | |
| (200 mg/kg $LD_{50}/5$) | 65 (± 1) | + 67 |
| 2nd experiment | | |
| Control | 39 (± 3) | |
| OC - 330 | | |
| (30 mg/kg or $LD_{50}/5$) | 67 (± 3) | + 71 |
| Vincamine | | |
| (200 mg/kg or $LD_{50}/5$) | 65 (± 2) | + 67 |

In conclusion at doses corresponding to 1/10 $LD_{50}$ for mice (p.o.) the compound OC-330 exerts an effect whose intensity is comparable to vincamine at 1/5 $LD_{50}$.

OC-330 is thus about two times more active than vincamine.

TABLE III

| Lot | OC - 331 Survival time (sec.) | Variation % |
|---|---|---|
| 1st experiment | | |
| Control | 39 (± 2) | |
| OC - 331 | | |
| (80 mg/kg or $LD_{50}/5$) | 122 (± 1) | + 214 |
| Vincamine | | |
| (200 mg/kg or $LD_{50}/5$) | 65 (± 3) | + 67 |
| 2nd experiment | | |
| Control | 39 (± 1) | |
| OC - 331 | | |
| (40 mg/kg or $LD_{50}/10$) | 80 (± 3) | + 105 |
| Vincamine | | |
| (200 mg/kg or $LD_{50}/5$) | 65 (+ 1) | + 67 |
| 3rd experiment | | |
| Control | 39 (± 1) | |
| OC - 331 | | |
| (20 mg/kg or $LD_{50}/20$) | 57 (± 4) | + 75 |
| Vincamine | | |

TABLE III-continued

| Lot | OC - 331 Survival time (sec.) | Variation % |
|---|---|---|
| (200 mg/kg or $LD_{50}/5$) | 52 (± 1) | + 59 |

In conclusion, at doses corresponding to 1/20 $LD_{50}$ for mice (p.o.), OC-331 exerts an effect comparable to vincamine at 1/5 $LD_{50}$. OC-331 is thus about four times more active than vincamine.

TABLE IV

| Lot | OC - 332 Survival time (sec.) | Variation % |
|---|---|---|
| Control | 35 (± 3) | |
| OC - 332 | | |
| (100 mg/kg or $LD_{50}/5$) | 76 (± 1) | + 117 |
| Vincamine | | |
| (200 mg/kg or $LD_{50}/5$) | 62 (± 4) | + 77 |

In conclusion, OC-332 at equally toxic dose when compared with vincamine exerts an effect about 1.5 times higher.

The above experiments show that the compounds of formula I have an anti-anoxic activity which is markedly stronger than vincamine.

These pharmaceutical properties cause the compounds of formula I to be therapeutically valuable in human and veterinary medicine, among others against cardiocirculatory, cerebro-vascular and respiratory insufficiencies.

For their therapeutical uses, the compounds of formula I may be administered either by digestive route in the form of capsules, tablets, pellets, dragees, cachets, solutions or suspensions or by parenteral route as buffered sterile solutions, prepared beforehand or extemporaneously, in which the active substance, base or salt, is present in an amount of 0.5 mg to 150 mg per unit. The daily dose may vary between 1 mg and 500 mg according to the disease.

It should be understood that many changes may be brought by the skilled art man to the process and products described hereinabove only as non-limiting examples and still remain within scope of this invention.

What I claim is:

1. A hexahydro-6-canthinone of the formula:

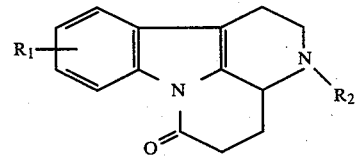

wherein $R_1$ represents a hydrogen atom, a methyl group or a halogen atom; whereas $R_2$ represents an alkyl group which contains 2–4 carbon atoms.

2. An hexahydro-6-canthinone according to claim 1 selected from
   3-ethyl-1,2,3,3a,4,5-hexahydro-6-canthinone (formula I: $R_1=H$; $R_2=C_2H_5$)
   3-propyl-1,2,3,3a,4,5-hexahydro-6-canthinone (formula I: $R_1=H$; $R_2=C_3H_7$)
   3-butyl-1,2,3,3a,4,5-hexahydro-6-canthinone (formula I: $R_1=H$; $R_2=C_4H_9$)
   3-isopropyl-1,2,3,3a,4,5-hexahydro-6-canthinone (formula I: $R_1=H$; $R_2=$iso $C_3H_7$)

10-methyl-3-ethyl-1,2,3,3a,4,5-hexahydro-6-canthinone (formula I: $R_1=CH_3$; $R_2=C_2H_5$)

10-chloro-3-ethyl-1,2,3,3a,4,5-hexahydro-6-canthinone (formula I: $R_1=Cl$; $R_2=C_2H_5$).

3. A pharmaceutical composition for use in human and veterinary medicine in treating cardio-circulatory, cerebrovascular and respiratory insufficiencies, containing an effective amount, from about 0.5 to 150 mg, of an active ingredient comprising at least one compound of the formula:

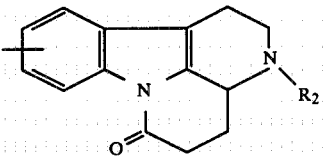

in which $R_1$ represents hydrogen, methyl or halo or a hydroxy group in the 8-position $R_2$ represents an alkyl group having from 1-4 carbon atoms together with a pharmaceutically acceptable carrier.

4. A pharmaceutical composition according to claim 3 wherein the active ingredient is selected from at least one of the following compounds:

3-ethyl-1,2,3,3a,4,5-hexahydro-6-canthinone (formula I: $R_1=H$; $R_2=C_2H_5$)

3-methyl-1,2,3,3a,4,5-hexahydro-6-canthinone (formula I: $R_1=H$; $R_2=CH_3$)

3-methyl-1,2,3,3a,4,5-hexahydro-8-hydroxy-6-canthinone (formula I: $R_1=$8-OH; $R_2=CH_3$)

3-propyl-1,2,3,3a,4,5-hexahydro-6-canthinone (formula I: $R_1=H$; $R_2=C_3H_7$)

3-butyl-1,2,3,3a,4,5-hexahydro-6-canthinone (formula I: $R_1=H$; $R_2=C_4H_9$)

3-isopropyl-1,2,3,3a,4,5-hexahydro-6-canthinone (formula I: $R_1=H$; $R_2=$iso $C_3H_7$)

10-methyl-3-ethyl-1,2,3,3a,4,5-hexahydro-6-canthinone (formula I: $R_1=CH_3$; $R_2=C_2H_5$)

10-chloro-3-ethyl-1,2,3,3a,4,5-hexahydro-6-canthinone (formula I: $R_1=Cl$; $R_2=C_2H_5$).

5. A pharmaceutical composition according to claim 4, wherein the active ingredient used in its base or pharmaceutically acceptable salt form is administered in unitary amounts of 0.5 mg to 150 mg per daily dose of 1 mg to 500 mg either by digestive route in the usual pharmaceutical forms of capsules, tablets, pellets, cachets, solutions or suspensions, or by parenteral route in the form of buffered sterile solution prepared beforehand or extemporaneously.

* * * * *